United States Patent [19]

Wunder et al.

[11] 4,372,878
[45] Feb. 8, 1983

[54] PROCESS FOR THE PREPARATION OF AN ALUMINUM SILICATE CATALYST FOR CONVERTING METHANOL CONTAINING WATER AND/OR DIMETHYL ETHER CONTAINING WATER INTO LOWER OLEFINS

[75] Inventors: Friedrich Wunder, Flörsheim; Ernst I. Leupold, Neu-Anspach; Horst Hachenberg, Walluf; Hans-Joachim Schmidt, Königstein; Klaus Unger, Seeheim-Jugenheim, all of Fed. Rep. of Germany

[73] Assignee: Hoechst Aktiengesellschaft, Frankfurt am Main, Fed. Rep. of Germany

[21] Appl. No.: 239,438

[22] Filed: Mar. 2, 1981

[30] Foreign Application Priority Data

Mar. 4, 1980 [DE] Fed. Rep. of Germany ....... 3008146

[51] Int. Cl.³ ............................................. B01J 29/06
[52] U.S. Cl. ................................................. 252/455 Z
[58] Field of Search ....................... 252/455 R, 455 Z

[56] References Cited

U.S. PATENT DOCUMENTS 3,682,996  8/1972  Kerr ................................. 260/448 C
4,145,315  3/1979  Rodewald ....................... 252/455 Z Primary Examiner—Carl F. Dees
Attorney, Agent, or Firm—Curtis, Morris & Safford

[57] ABSTRACT

The process according to the invention comprises silanizing an aluminum silicate and then heating the product to 300° to 600° C. in the presence of oxygen or of gases containing oxygen. A highly selective catalyst which can be regenerated very many times is thereby obtained.

2 Claims, No Drawings

PROCESS FOR THE PREPARATION OF AN ALUMINUM SILICATE CATALYST FOR CONVERTING METHANOL CONTAINING WATER AND/OR DIMETHYL ETHER CONTAINING WATER INTO LOWER OLEFINS

Processes for the preparation of lower olefins from methanol and/or dimethyl ether on aluminum silicate catalysts are described in German Offenlegungsschrift No. 2,755,229, U.S. Pat. Nos. 4,062,905, 3,911,041, 4,079,095, 3,979,472 and German Offenlegungsschrift No. 2,615,150. A common characteristic of all these catalysts is that they must be regenerated periodically, that is to say they must be freed from the by-products formed, which can already be effected with air at relatively low temperatures of 300° C. to 500° C., and most advantageously at the reaction temperature itself. If dimethyl ether or methanol which contains no water or only a very little water is used, these catalysts can be regenerated very many times without a reduction in efficiency or selectivity occurring. However, if conversion is incomplete, a methanol/water mixture is obtained, in addition to lower olefins. The methanol contained in this mixture must be recovered; however, without considerable expenditure, only methanol containing water is obtained in the distillation. The presence of water indeed has no advantageous effect on the selectivity for lower olefins, but it is found that in this case some aluminum silicates lose a significant amount of activity under the reaction conditions and can be regenerated again only a few times. Careful dehydration of the methanol before recycling indeed solves this problem, but means a high energy consumption.

There was thus the object of preparing an aluminum silicate catalyst for the conversion of methanol containing water and/or dimethyl ether containing water into lower olefins, which can be regenerated very many times. Surprisingly, this can be achieved by silanizing an aluminum silicate and then heating the product in the presence of oxygen.

Silanization of silicic acids and silicates has already been described several times, for example: G. Erdel and K. Unger, J. Vac. Sc. Technol. 11 (1), (1974), page 429 or A. V. Kieselev et al, J. Colloid, Interface Sci. 69, (1979), page 148.

Application of this silanization to zeolites is described in U.S. Pat. No. 3,682,996, the resulting reduced absorption properties leading to an increased selectivity in the case of alkylation, hydrocarbon cracking reactions, hydrocracking and isomerization. However, subsequent heating in the presence of oxygen is not described.

A process has now been found for the preparation of an aluminum silicate catalyst for converting methanol containing water and/or dimethyl ether containing water into lower olefins, which comprises silanizing an aluminum silicate and then heating the product to 300° C. to 600° C. in the presence of oxygen or of gases containing oxygen.

Surprisingly, silanization without the subsequent heat treatment according to the invention causes a reduction in selectivity, and a highly selective catalyst which can be regenerated very many times is only obtained by this subsequent treatment.

It is possible to use, for example, the naturally occurring or synthetic crystalline aluminum silicates, such as the molecular sieves known as faujasites, zeolites, chabazites, analcite, gismondite, gmelinite, natrolite, mordenites and erionites. The chabazite/erionite mixture which occurs naturally in large amounts is advantageously used. Furthermore, the customary, amorphous, acid cracking catalysts which in general contain between 13 and 25% by weight of aluminum oxide and 75 to 87% by weight of silicic acid are also suitable.

In the case of the amorphous as well as the crystalline aluminum silicates, it is expedient to use those with pore diameters of 5 A or more.

Suitable silanizing agents are all the silanes which carry one or more reactive groups which react with hydroxyl groups. Compounds of the general formula

in which n=1, 2 or 3, R is an alkyl radical with up to 5 C atoms and X is halogen, and compounds such as hexamethyldisilazane (CH$_3$)$_3$Si-NH-Si(CH$_3$)$_3$, N,O-bis-trimethylsilylacetamide

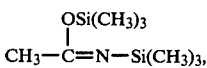

N,N-bis-trimethylsilyltrifluoroacetamide

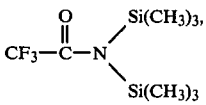

trimethylsilyl azide (CH$_3$)$_3$Si-N$_3$, N-trimethylsilyldiethylamine (CH$_3$)$_3$Si-N(CH$_2$H$_5$)$_2$, N-trimethylsilylimidazole

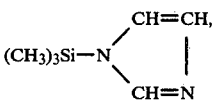

tetramethyl ortho silicate Si(OCH$_3$)$_4$ and tetraethyl ortho silicate Si(OC$_2$H$_5$)$_4$ are preferred.

The compounds (CH$_3$)$_3$SiCl and (CH$_3$)$_3$SiBr, and the pure or mixed methyl and ethyl compounds, such as (C$_2$H$_5$)$_3$SiCl, (C$_2$H$_5$)$_2$CH$_3$SiCl and (CH$_3$)$_2$C$_2$H$_5$SiCl, as well as the nitrogen-containing compounds mentioned above are particularly suitable.

To prepare the catalysts according to the invention, the aluminum silicates are in general dried and then brought into contact with gaseous or liquid silanes. Excess silane is then removed, in particular by washing out with a solvent (such as ether) or by heating in vacuo. The catalyst is then activated by heating to 300° C. to 600° C., preferably 350° C. to 500° C., in the presence of oxygen or of a gas containing oxygen. Before the silanization or after the activation, the aluminum silicate can be charged with manganese, preferably by means of ion exchange, but also in some cases by simple impregnation with a manganese salt. In the case of such doping with manganese, the manganese content is in general up to 10%. It has the effect of increasing the selectivity for lower olefins.

Water, methanol, formamide, dimethylformamide or mixtures thereof, in particular water, are preferred solvents for the manganese salts. Possible manganese salts are all the readily soluble and readily accessible salts, for example the formate, acetate, propionate, butyrate, lactate, citrate, tartrate, malate, chloride, bromide, nitrate and sulfate.

If molecular sieves are used, one of the methods of impregnation with a metal cation which are customary for these materials can be used; this can be an exchange of the cations originally present on the molecular sieve for manganese, or it can also be prior conversion of the molecular sieve into the acid form, followed by treatment with the solution of a manganese salt.

For a high selectivity, it has furthermore frequently proved to be advantageous also to use other elements as co-catalysts. Suitable elements are those which are monovalent, divalent or trivalent in their compounds, such as, for example, the alkali metals (in particular lithium, sodium and potassium), the alkaline earth metals (in particular magnesium, calcium and barium), zinc, cadmium, lanthanum, rare earths (such as praseodymium, neodymium, samarium, gadolinium or mixtures thereof, such as didymium) and beryllium.

These metal ions which act as co-catalysts can be applied at the same time or successively; however, in the case of simultaneous solution, the reciprocal effect on solubility must be taken into consideration, that is to say, for example, sulfates are unsuitable when calcium or barium is used.

In the preparation of lower olefins from methanol using the catalyst according to the invention, it is possible either for the methanol to be passed directly over the catalyst (in which case the methanol can have a high water content) or for all or some of the methanol first to be converted into dimethyl ether and water on a customary dehydrogenation catalyst, such as, for example, aluminum oxide or aluminum silicate, and for the ether, by itself or together with the water present or formed and if appropriate with unreacted methanol, then to be passed over the catalyst. However, it is also possible to use mixtures of methanol and dimethyl ether, or dimethyl ether by itself, as the starting substance.

The starting components methanol and/or dimethyl ether can also be diluted with inert gases for use in the reaction. Nitrogen and carbon dioxide, for example, are suitable for reducing the partial pressure. However, for this purpose, the reaction can also be carried out under a reduced pressure of down to 0.1 bar.

The water content of the starting materials can vary within wide limits, that is to say from 0 up to about 80% of water, but higher amounts of water result in higher evaporation and distillation costs, so that the upper limit of the water content is determined by economic considerations.

The reaction temperature is in general between 300° C. and 500° C., preferably between 380° C. and 420° C. If the reaction conditions are chosen such that only incomplete conversion of methanol and/or dimethyl ether is achieved, the unreacted portions can be separated off and recycled. The alkenes prepared on the catalysts according to the invention can be separated from the alkanes formed as a by-product and from one another by the customary methods, for example by distillation.

A process which permits particularly selective and hence economic preparation of industrially important lower alkenes from methanol and/or dimethyl ether in the presence of large amounts of water is thus available. In view of the state of the art, it is particularly surprising that the silanization without subsequent activating heating has an adverse effect on the efficiency and selectivity and that the catalysts only achieve their outstandingly selective and stable properties after activation with oxygen or gases containing oxygen at elevated temperatures, although the amount of silicon applied changes the ratio Al:Si in the total particle only by less than 0.5%.

The following examples illustrate the process according to the invention.

COMPARISON EXAMPLE 1

(Chabazite/Erionite Impregnated with Manganese)

300 ml of a commercially available chabazite/erionite mixture in the form of extruded strands is covered with a layer of 300 ml of saturated aqueous manganese acetate solution and, after 48 hours, is washed out with water and dried. 202 g of catalyst containing 3.6% by weight of manganese are obtained. 89.1 g of methanol per hour are passed over this catalyst at 400° C. 25 l of gas consisting of 26.6% by weight of ethylene, 27.9% by weight of propylene, 4.6% by weight of butenes, 6.7% by weight of methane, 1.3% by weight of ethane, 17.4% by weight of propane, 3.0% by weight of butane, 0.5% by weight of other compounds and 12.0% by weight of dimethyl ether, as well as 9.2 g of methanol and 43.3 g of water are obtained per hour. This corresponds to a methanol conversion of 89.6%, a selectivity for $C_2$–$C_4$-olefins of 68.9% and a selectivity for $C_2$–$C_4$-hydrocarbons of 93%, if the dimethyl ether formed and the unreacted methanol are recycled.

When its efficiency decreases, the catalyst is regenerated by passing over air at 430° C., whereupon the efficiency of the fresh catalyst is achieved. Even after 26 regenerations, no exhaustion of the catalyst is observed.

COMPARISON EXAMPLE 2

Comparison Example 1 is repeated, with the sole difference that water is added to the starting methanol. If 87.4 g of methanol and 43.1 g of water are fed in per hour, 26 l of a hydrocarbon gas containing 30.0% by weight of ethylene, 29.4% by weight of propene, 5.4% by weight of butenes, 7.3% by weight of methane, 1.2% by weight of ethane, 13.2% by weight of propane, 2.2% by weight of butanes, 0.3% by weight of other compounds and 11.3% by weight of dimethyl ether, as well as 7.8 g of methanol and 86.0 g of water are obtained per hour. This corresponds to a methanol conversion of 91.1%, a selectivity for $C_2$–$C_4$-olefins of 74.2% and a selectivity for $C_2$–$C_4$-hydrocarbons of 92.5%, if the dimethyl ether and the unreacted methanol are recycled.

Hydrocarbon selectivities of only 12% are already achieved after the third regeneration (carried out as in Comparison Example 1), that is to say that water in the starting material irreversibly damages the catalyst.

COMPARISON EXAMPLE 3

300 ml of the catalyst described in Comparison Examples 1 and 2 are dried at 200° C. in vacuo for 12 hours and covered with a layer of trimethylchlorosilane under an inert gas atmosphere, and the mixture is boiled under reflux at 50° C. in a rotary evaporator. After 6 hours, the excess trimethylchlorosilane is washed out with analytical grade dimethyl ether and the catalyst is dried in an inert gas atmosphere at 120° C. for 12 hours. Under the conditions of Comparison Example 2, when 86.3 g of methanol and 44.8 g of water are fed in per hour, 26 l of a hydrocarbon mixture composed of 19.7% by weight of ethylene, 24.3% by weight of propylene, 7.4% by weight of butenes, 8.6% by weight of methane, 1.7% by weight of ethane, 21.8% by weight of propane, 4.3% by weight of butane, 0.7% by weight of other compounds and 11.6% by weight of dimethyl ether, as well as 91 g of water and 0.5 g of methanol are obtained per hour. This corresponds to a selectivity for $C_2$–$C_4$-olefins of 60%, a selectivity for $C_2$–$C_4$-hydrocarbons of 90.8% and a conversion, relative to methanol, of 99.4%.

EXAMPLE 1

The catalyst prepared as in Comparison Example 3 is treated with air at 400° C. for 12 hours. 98.3 g of methanol and 53.2 g of water per hour are passed over this catalyst under the conditions of Comparison Example 3. 23 l of a hydrocarbon mixture composed of 39.3% by weight of ethylene, 29.7% by weight of propylene, 7.8% by weight of butenes, 6.7% by weight of methane, 1.5% by weight of ethane, 6.9% by weight of propane, 3.6% by weight of butane, 0.8% by weight of other compounds and 3.7% by weight of dimethyl ether, as well as 107 g of water and 1.8 g of methanol are obtained per hour. This corresponds to a conversion, relative to methanol, of 98.2%, a selectivity for $C_2$–$C_4$-olefins of 81.2% and a selectivity for $C_2$–$C_4$-hydrocarbons of 93.4%.

After 54 regenerations, carried out as in Comparison Example 1, virtually unchanged values are obtained.

EXAMPLE 2

400 ml = 265 g of a commercially available, naturally occurring chabazite/erionite mixture are doped with 2.4% by weight of manganese and 1.2% by weight of rare earths (mixture) by ion exchange, dried at 200° C. in vacuo for 12 hours and then exposed to the partial vapor pressure of triethylchlorosilane at 80° C. for 24 hours. Excess silane is then evaporated off in vacuo, and the catalyst is then activated with air at 410° C. 210 ml of 50% strength water-containing methanol per hour are passed over this catalyst at 390° C. and under 1 bar. 27.5 l of reaction gas composed of 35.5% by weight of ethylene, 38.3% by weight of propene, 6.4% by weight of butenes (predominantly 2-butene), 2.6% by weight of methane, 0.6% by weight of ethane, 4.2% by weight of propane, 3.4% by weight of butane, 0.4% by weight of other compounds and 8.6% by weight of dimethyl ether, as well as 148 g of water and 4.7 g of methanol are obtained per hour. This corresponds to a selectivity for ethylene of 39.1%, a selectivity for propene of 42.1% and a selectivity for butenes of 7.0%. $C_2$–$C_4$-olefins are formed with a total selectivity of 88.2% and $C_2$–$C_4$-hydrocarbons are formed with a selectivity of 97.0%, dimethyl ether being calculated as methanol.

After 48 regenerations, the catalyst has a virtually unchanged efficiency and selectivity.

EXAMPLE 3

250 g of a commercially available, naturally occurring chabazite/erionite mixture are subjected to ion exchange with manganese-II ions, washed out thoroughly and dried at 300° C. in vacuo for 12 hours. The mixture is then silanized with tetramethyl silicate at 50° C. and, after 12 hours, the excess silicate is removed in vacuo. After activation for 3 hours in air at 450° C., 260 ml/hour of 50% strength water-containing methanol are passed over the catalyst at 400° C. 35 l of reaction gas containing 23.5% by weight of ethylene, 31.5% by weight of propene, 5.6% by weight of butenes, 3.9% by weight of methane, 0.7% by weight of ethane, 5.7% by weight of propane, 2.5% by weight of butane, 0.4% by weight of other compounds and 26.2% by weight of dimethyl ether, as well as 176 g of water and 5.8 g of methanol are obtained per hour. This corresponds (calculating dimethyl ether as methanol) to a selectivity for ethylene of 32.4%, a selectivity for propene of 43.4% and a selectivity for butenes of 7.6%, the $C_2$–$C_4$-olefins together being formed with a selectivity of 83.4% and the $C_2$–$C_4$-hydrocarbons being formed with a selectivity of 95.1%. After 35 regenerations, the catalyst still has the same efficiency and selectivity.

EXAMPLE 4

242 g of a commercially available, naturally occurring chabazite/erionite mixture are subjected to ion exchange with manganese, dried in vacuo, silanized in acetonitrile with hexamethyldisilazane, washed out with pure acetonitrile, dried, and activated in air at 450° C. The finished catalyst contains 2.3% by weight of manganese. 380 ml of 66.7% strength water-containing methanol per hour are passed over this catalyst at 410° C. 65 l of a reaction gas consisting of 32.5% by weight of ethylene, 26.9% by weight of propene, 3.5% by weight of butenes, 5.4% by weight of methane, 1.0% by weight of ethane, 11.7% by weight of propane, 1.4% by weight of butane, 1.1% by weight of other compounds and 16.4% by weight of dimethyl ether, as well as 220 g of water and 12.6 g of methanol are obtained per hour. This corresponds to a selectivity for ethylene of 39.8%, a selectivity for propene of 32.9% and a selectivity for butenes of 4.3% (dimethyl ether having been calculated as methanol), that is to say the $C_2$–$C_4$-olefins are together formed with a selectivity of 77% and the $C_2$–$C_4$-hydrocarbons are formed with a selectivity of 93.5%. After 49 regenerations, the catalyst still has the same activity and selectivity.

EXAMPLE 5

167 g of a synthetic faujasite in the form of extruded strands is washed with water and carbon dioxide until the washings are neutral and is then covered with a layer of saturated manganese acetate solution and, after 48 hours, washed with water until manganese can no longer be detected in the washing. After drying at 200° C. in vacuo, the catalyst is silanized with triethylorthosilicate and then activated at 350° C. in air. The finished catalyst contains 4.6% by weight of manganese.

175 ml of 50% strength water-containing methanol per hour are passed over this catalyst at 410° C. 22 l of a reaction gas consisting of 18.3% by weight of ethylene 19.9% by weight of propene, 12.2% by weight of butenes, 11.6% by weight of methane, 1.9% by weight of ethane, 18.3% by weight of propane, 10.6% by weight of butane, 0.8% by weight of other compounds and 6.4% by weight of dimethyl ether, as well as 120 g of water and 5.3 g of methanol are obtained per hour. This corresponds (calculating dimethyl ether as methanol) to a selectivity for ethylene of 19.9%, a selectivity for propene of 22.2%, a selectivity for butenes of 13.3%, a selectivity for methane of 11.0%, a selectivity for ethane of 2.0%, a selectivity for propane of 19.0% and a selectivity for butanes of 11.2%, that is to say the $C_2$–$C_4$-olefins are formed with a selectivity of 55.4% and the $C_2$–$C_4$-hydrocarbons are formed with a selectivity of 87.6%. After 26 regenerations, the efficiency and selectivity have not changed.

We claim:

1. A process for the preparation of a crystalline zeolite catalyst for converting methanol containing water and/or dimethyl ether containing water into lower olefins, which comprises silanizing a naturally occurring chabazite/erionite mixture and subsequently heating the product to 300° C. to 600° C. in the presence of oxygen or of gases containing oxygen.

2. A process as claimed in claim 1, wherein the heating temperature is 350° C. to 500° C.